(12) United States Patent
Biancarelli

(10) Patent No.: US 11,759,607 B1
(45) Date of Patent: Sep. 19, 2023

(54) DISTAL CLOSING CLOT RESISTANT CENTRAL VENOUS CATHETER

(71) Applicant: Joseph Paul Biancarelli, Ulster, PA (US)

(72) Inventor: Joseph Paul Biancarelli, Ulster, PA (US)

( * ) Notice: Subject to any disclaimer, the term of this patent is extended or adjusted under 35 U.S.C. 154(b) by 177 days.

(21) Appl. No.: 16/873,387

(22) Filed: Apr. 6, 2020

Related U.S. Application Data

(60) Provisional application No. 62/920,023, filed on Apr. 10, 2019.

(51) Int. Cl.
*A61M 25/00* (2006.01)

(52) U.S. Cl.
CPC ........ *A61M 25/007* (2013.01); *A61M 25/003* (2013.01)

(58) Field of Classification Search
CPC .............. A61M 25/007; A61M 25/003; A61M 2025/0036; A61M 2025/0037; A61M 2025/004
See application file for complete search history.

(56) References Cited

U.S. PATENT DOCUMENTS

2010/0100055 A1\* 4/2010 Mustapha ......... A61M 25/0075
604/525
2013/0274711 A1\* 10/2013 O'Day .................. A61M 39/08
604/508

\* cited by examiner

*Primary Examiner* — James D Ponton

(57) ABSTRACT

A multiple lumen central venous catheter with the lumens exit ports on the distal sides of the catheter; enclosed in a separate casing that has exit ports in the walls at its distal end; that allows the enclosed catheter to rotate in the casing, allowing the exit ports in the catheter to align or non-align to open and close the individual lumens at the distal end.

1 Claim, 10 Drawing Sheets

PRIOR ART
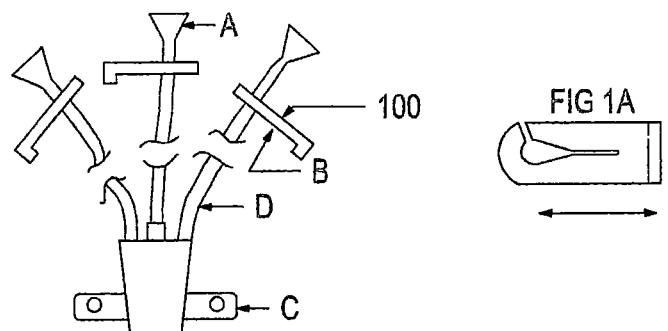
FIG 1A
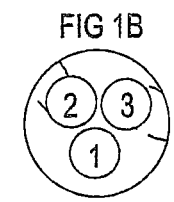
FIG 1B
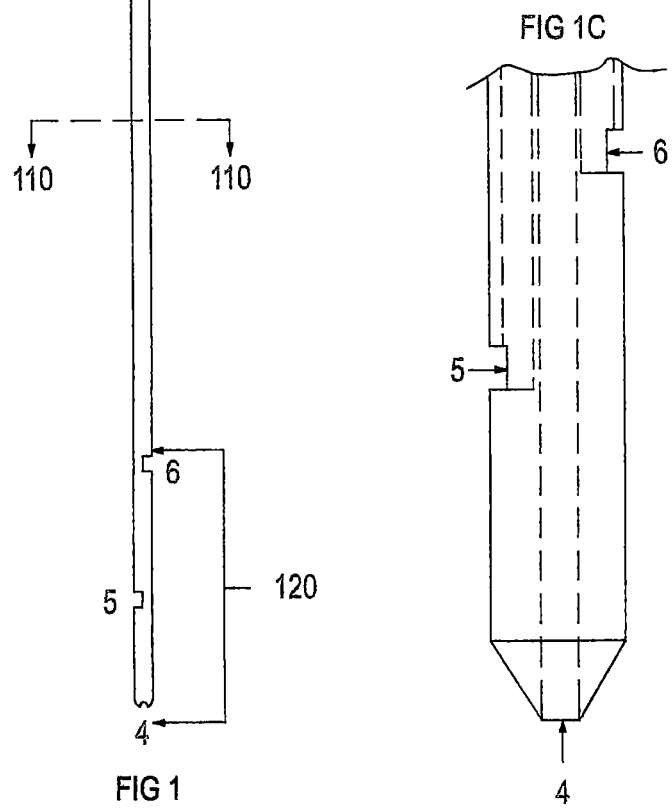
FIG 1
FIG 1C

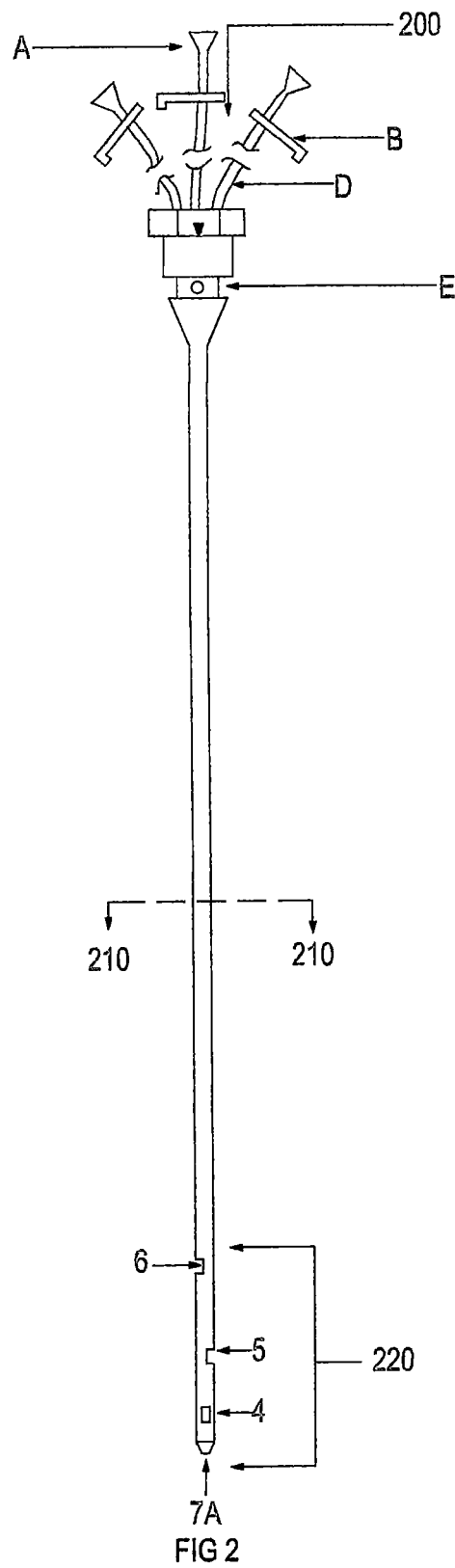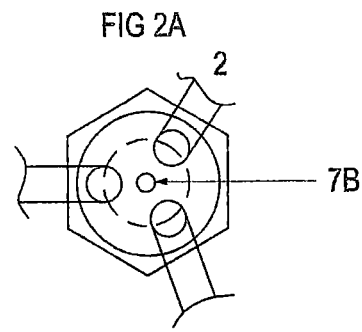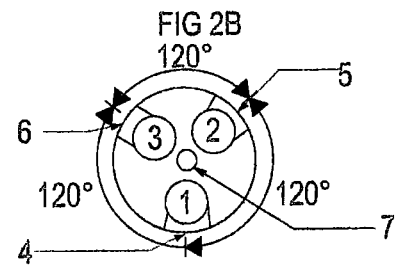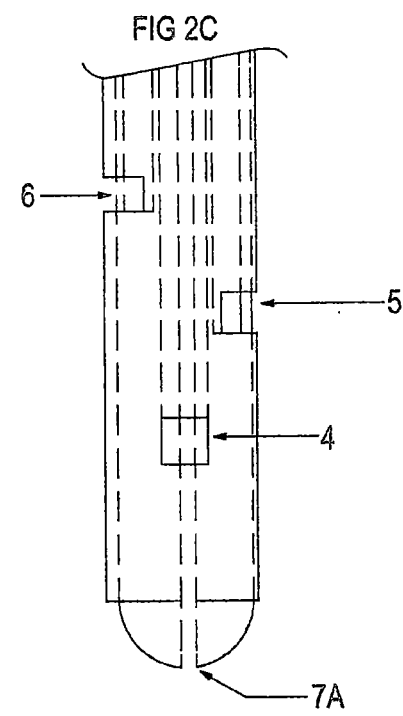
FIG 2
FIG 2A
FIG 2B
FIG 2C

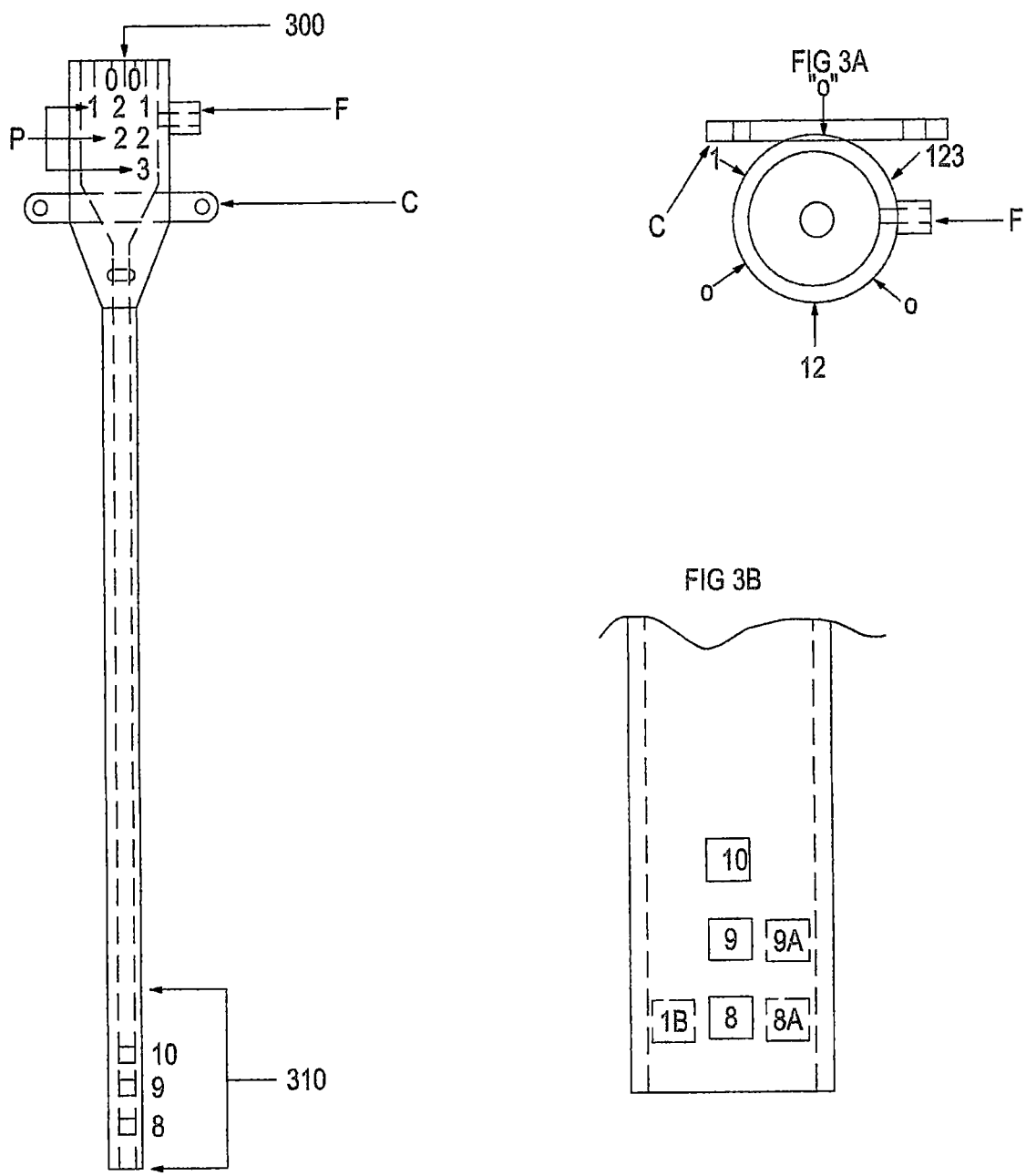

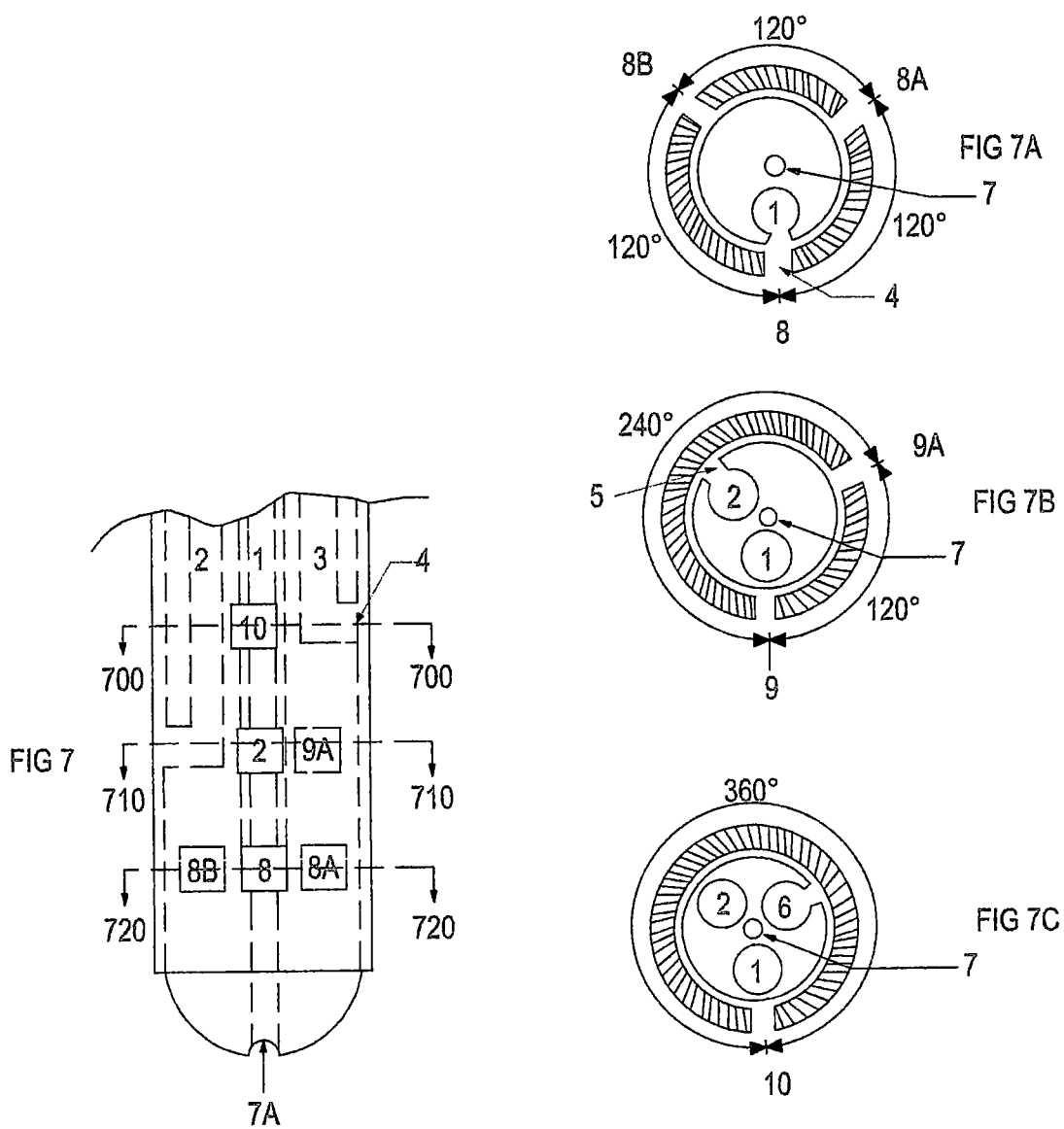

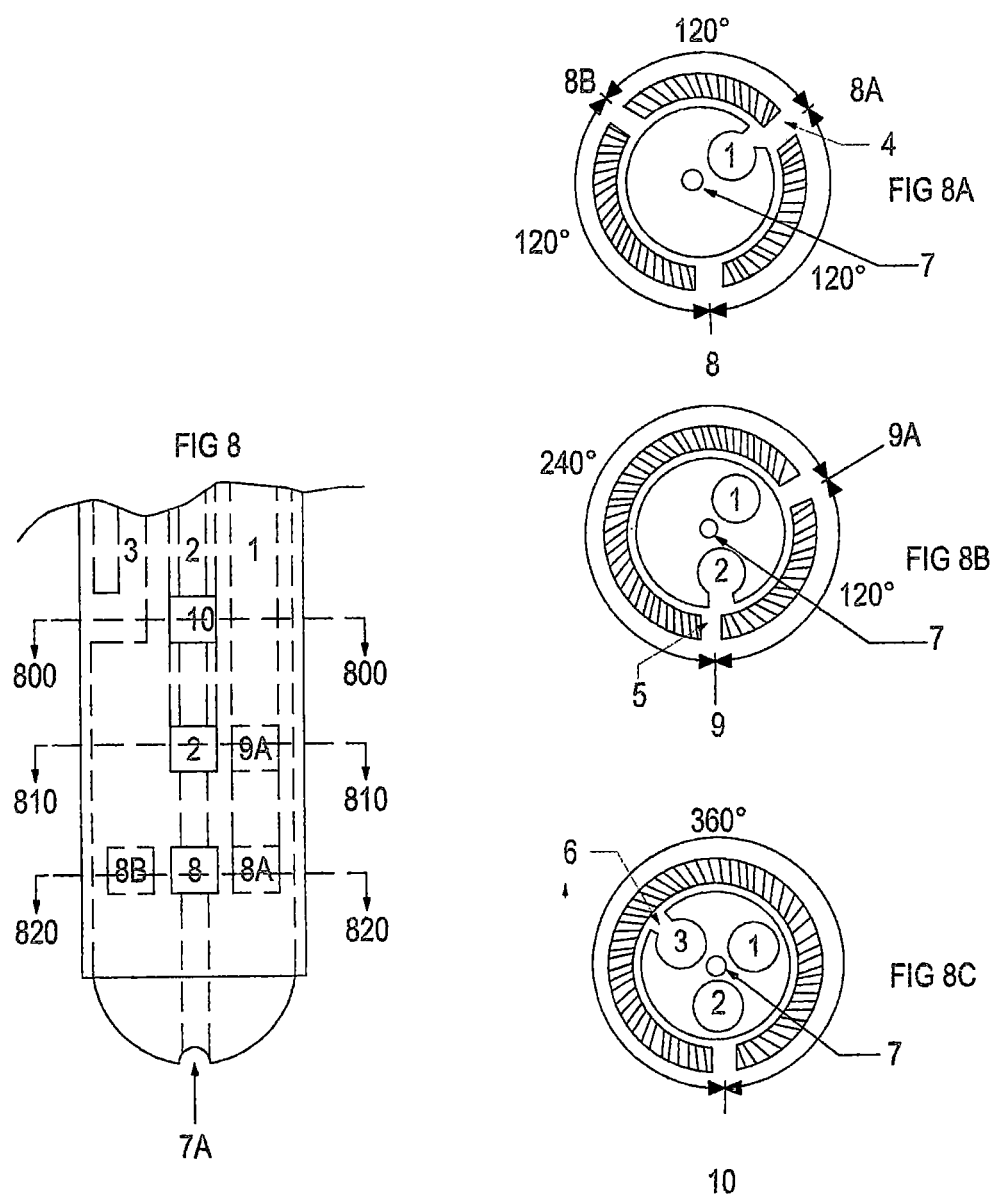

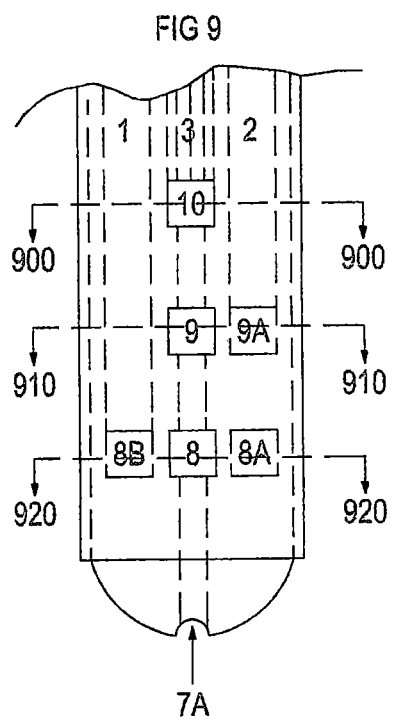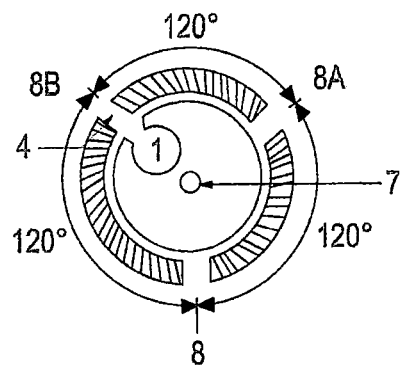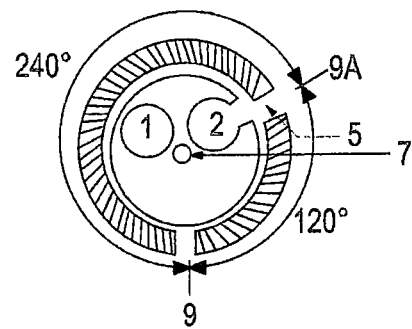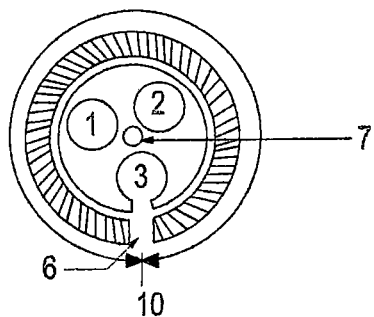

DISTAL CLOSING CLOT RESISTANT CENTRAL VENOUS CATHETER

BACKGROUND

Central venous catheters are a type of medical device. They are used to access a large central vein, i.e. subclavian, to allow frequent I.V. infusions and blood draws during the course of a patient's therapy to avoid constantly subjecting the patient to repeated blood draws or risking damaging a small vein with constant I.V. infusion.

These catheters are inserted into the vein at the bedside using sterile technique. To install, a guide wire is used. This guide wire is over twice the length of the catheter. The surgeon accesses the large vein, then threads one end of the guidewire a short distance into the vein.

The other end of this guide wire is placed into the lumen at the extreme distal tip of the catheter (Sheet 1, FIG. 1C "4") and then threaded through the entire length of the catheter until the guide wire emerges from the proximal end of the catheter lumen (Sheet 1, FIG. 1 "A").

The surgeon holds this end of the guidewire with one hand, and then slides the catheter down the guidewire into the vein. The guide wire is then removed, and the catheter is stitched to the skin using the two holed flanges on the catheter (sheet 1, FIG. 1"C"). The catheter is then ready for use.

Central venous catheters can be made with multiple, separate lumens to allow multiple medications and infusions to be used at the same time through the same catheter. The most commonly used type has three separate lumens, or a "triple lumen catheter".

The problem with all current central venous catheters is that they have provision to close their lumens only at the proximal end, leaving the lumens open at the distal end, allowing blood to migrate into the lumen during periods of non-use. The blood then stagnates and forms a clot in the lumens, rendering the catheter useless and requiring replacement.

In this patent application, the proximal end of the catheter is outside the body and is where the I.V. medication lines attaches, and the distal end is in the vein, exposed to the blood stream.

BRIEF SUMMARY OF INVENTION

This new catheter design addresses the issue of clotting in the distal end of the lumens by using two parts, the catheter proper and an external casing. This design can be used on multiple lumen catheters of any number. The following description and drawings show the design being applied to the triple lumen catheter, as this type is, by far, the most commonly used type in clinical practice.

The catheter/casing idea is not new to the art, PN #U.S. Pat. No. 6,508,790B1, U.S. Pat. Nos. 3,575,230, and 4,913,704 all reference the idea of using a separate casing to protect the incision site or to easily change the catheter when it becomes clotted.

Instead, this design allows the catheter to move up and down (proximally) rotate inside the casing, allowing side mounted lumens exit holes to be covered by the casing when not being used and be closed to the blood stream distally. This will avoid the clotting problem altogether and eliminate the need for constant replacement. The catheter/casing is pre-assembled and sterilized at the factory and installed using a guide wire, the same as a conventional catheter.

In this new design the lumens exit at the distal sides only, but not at the distal tip. This is done because the casing must be able to cover and uncover the lumens exit holes to close the lumens distally. If the catheter is to be installed with a guide wire, it would have to be inserted in the side of the catheter for placement in the vein.

If this is done, the guide wire would be at an angle to the catheter, instead of being aligned with the catheter's axis, as it would be if it had a lumen that opens at the extreme tip like a conventional catheter (Sheet 1, FIG. 1 "4"). This would make installation difficult, if not impossible.

If one of the lumens in the new catheter (Sheet 2, FIG. 2) was to exit at the distal tip, like a conventional catheter (Sheet 1, FIG. 1) that lumen would be subject to clotting as that lumen would not be covered by the casing.

In order to have all lumens seal at the distal end, a "guide wire lumen" can be incorporated in all variants of this design. This lumen can be made much smaller in diameter than the other usable lumens, and sized to fit a small diameter guide wire.

This "guide wire lumen" is open at the distal tip and runs the entire length of the catheter but terminates at the proximal end with a simple exit hole (sheet 2, FIG. 2a, 7b). This exit hole is closed after the guidewire is withdrawn with a simple pin or plastic plug (sheet 2, FIG. 2b, "7").

During installation, the surgeon slides the catheter over the guide wire using the "guide wire lumen" because the catheter is now aligned with the guide wire along the catheter's axis, it can slide into the vein over the guide wire as in a conventional catheter. Once the catheter is installed, the guide wire is removed and the "guide wire lumen" is plugged at the proximal end and not used again.

In summary, installation of this new catheter design is no more difficult than current, and because of it's casing it is more resistant to kinking and should be in fact, easier to install.

This new catheter design is to be able to open and close it's lumens "sequentially", i.e. lumen 1 open, and lumens 2 and 3 closed (Position "1"); lumens 1 and 2 open and 3 closed (Position 1,2"); or lumens 1, 2, and 3 open (Position "1, 2, 3") as well as all lumens closed (Position "0").

This allows opening the lumens for use but keeping the lumens not being used closed to the blood stream, and is a desirable feature.

As stated previously the catheter and casing can work by rotating the catheter in its casing. For this application the rotating catheter is called the "rotational variant".

BRIEF DESCRIPTION OF DRAWINGS

Sheet 1 shows a triple lumen catheter of the current art. FIG. 1 shows the entire catheter in profile. Luer-Lock connectors are labeled "A", IV tubing pinch-locks are labeled "B", I.V. tubing is labeled "D", stitched ears are labeled "C". FIG. 1A shows a view of the pinch locks taken along line 100 in FIG. 1. FIG. 1B is a cross section view taken along line 110-110 of FIG. 1. The infusion lumens are labeled 1, 2, and 3. FIG. 1C shows an enlarged view of an area of the distal catheter taken along line 120 of FIG. 1. Exit ports of the infusion lumens are labeled 4, 5, and 6.

Sheet 2 shows the new catheter portion of this application. FIG. 2 shows an overall view of the new catheter. Luer-Lock connectors are labeled "A". IV tubing pinch locks are labeled "B", and the IV tubing connecting the Luer-Locks to the infusion lumens in the catheter is labeled "D". A circular lock-in track is new for this application and is labeled "E". FIG. 2A is a view of the catheter taken along line 200 on FIG. 2. The opening for the central guide wire lumen is labeled 7 B. FIG. 2B is a cross section view taken along line 210-210 on FIG. 2. Infusion lumens are labeled 1, 2, and 3. The central guide wire lumen is new for this application and labeled 7. FIG. 2C is an enlarged view of the area of the distal end of the catheter taken along line 220 in FIG. 2. Infusion lumens exit ports are labeled 4, 5, and 6. Guide wire lumen exit port is labeled 7A.

Sheet 3 is a drawing of the casing portion of the application. FIG. 3 shows the overall view of the casing. The stitch ears are located on the casing and labeled "C", the locking pin collar is labeled "F". The engraved witness marks on the proximal end of the casing are labeled "P". The witness marks 1, 12 and 123 are shown in the same plane for clarity, but are radially arranged around the proximal casing 120° from each other. The 0 witness marks are arranged radially around the casing as well, 120° apart, and separated from witness marks 1, 12, 123 by 60°. FIG. 3A is a view of the casing taken along line 300 in FIG. 3 and shows the angular relationship of the witness marks. FIG. 3B shows an enlarged view of the area of the distal casing taken along line 310 in FIG. 3, showing the position of the casing ports along the long axis of the casing. Port 10 is the most proximal, ports 9 and 9A is distal to port 10, and ports 8, 8A, and 8B are distal to ports 9 and 9A.

Sheet 4 shows the assembled catheter and casing with catheter rotated in the casing to the "1" witness mark. At this position infusion lumen 1 is open to the bloodstream at the distal end, and lumens 1 and 2 are closed to the bloodstream at the catheter 1 casings distal end.

Sheet 5 shows the distal tip of the catheter.

Sheet 6 is a view of the distal tip of the casing showing the ports.

Sheet 7 shows the assembled catheter and casings distal end with the catheter rotated in the casing to the "1" witness mark, open lumen 1 to the bloodstream. FIG. 7 shows the distal area of the catheter and casing port 10, 9 and 8 are facing the viewer, ports 9A, 8A and 8B are out of view and are represented by dashed lines. FIG. 7A shows a cross section taken along line 720-720. In FIG. 7A infusion lumen port 4 is aligned with casing port 8 and open to the bloodstream catheter. Ports 5 and 6 are proximal to this cross section. FIG. 7B is a cross section taken along line 710-710. In FIG. 7 catheter port 5 is covered by the casing and closed to the bloodstream. FIG. 7C is a cross section taken along line 700-700. In FIG. 7 infusion port 6 is covered by the casing wall and closed to the bloodstream.

Sheet 8 shows the distal end of the assembled catheter and casing with catheter rotated to the witness mark "12" opening lumen 1 and 2 to the bloodstream. FIG. 8 shows the distal end of the catheter and casing ports 10, 9 and 8 are facing the viewer. Ports 9B, 8A and 8B are out of view and represented by dashed lines. FIG. 8A is a cross section taken along line 820-820. In FIG. 8A lumen port 4 is aligned with casing port 8A and open to the bloodstream. Lumen ports 5 and 6 are proximal. FIG. 8B is a cross section taken along line 810-810. In FIG. 8B lumen port 5 is aligned with casing port 9 and open to the bloodstream. Lumen port 6 is proximal to this lumen. FIG. 8C is a cross section taken along line 800-800. Lumen port 6 is covered by the casing wall and closed to the bloodstream.

Sheet 9 shows the distal end of the assembled catheter and casing with the catheter rotated in the casing to the witness mark "123", opening infusion lumen 1, 2 and 3 to the bloodstream. FIG. 9 is a view of the distal tip of the catheter and casing ports 10, 9 and 8 are facing the viewer. Casing ports 9A, 8A and 8B are out of view and represented by dashed lines. FIG. 9A is a cross section taken along line 920-920. Lumen port 4 is aligned with casing port 8B and open to the bloodstream. Infusion lumen ports 5 and 7 are proximal to this level. FIG. 9B is a cross section taken along line 910-910. Lumen port 5 is aligned with casing port 9A and open to the bloodstream. Lumen port 6 is proximal to this level. FIG. 9C is a cross section taken along line 900-900. Lumen port 6 is aligned with casing port 10 and open to the bloodstream.

Sheet 10 is a view of the proximal end of the assembled catheter and casing.

Figure 4:
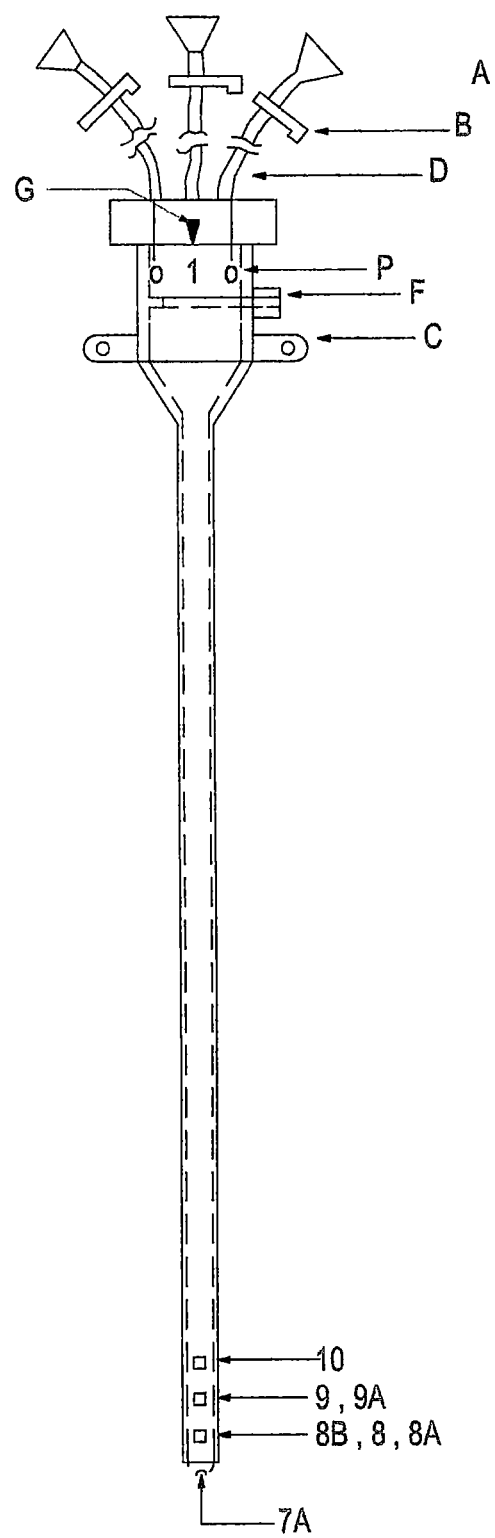
FIG. 4 shows the overall view of the assembled catheter and casing Luer-Lock connectors, pinch locks and IV tubing are labeled A, B, and D. Casing witness marks and stitch ears are labeled "P" and "C", the witness mark on the catheter is "G". At the distal end the locations of casing ports 10, 9, 9A, 8, 8A and 8B are shown in their positions on the distal casing and are arranged in three levels. The most proximal contains port 10, distal to this level ports 9, 9A are located and separated 120° from each other on the radial plane. Most distal levels contain ports 8, 8A, and 8B separated from each other by 120° on the radial plane.

Description and Use of Catheter in Detail

Sheet 1, FIG. 1 shows a triple lumen catheter of the current art. These catheters are molded out of plastic that can be sterilized. The proximal head is hard, the catheter body is made to be soft and flexible. The proximal head has two "stitch ears" (Sheet 1, FIG. 1 "C") that are flanges with holes where sutures can be passed through it and stitched to the skin, anchoring the catheter to the skin.

The three lumens terminate at the proximal end in I.V. tubing (Sheet 1, FIG. 1 "D") which is about three inches in length, and terminate proximally in "Luer-lock" connectors or similar devices (Sheet 1, FIG. 1 "A"). To connect peripheral I.V. medication lines to the catheter. Sliding "pinch locks" (Sheet 1, FIG. 1 "B") are located on the I.V. tubing, and by sliding the lock in the direction of the arrow in Sheet 1, FIG. 1 "B", "pinch" the flexible tubing closed and seal the lumen at that point (the proximal end). These are used on all three lumens.

The three lumens, labeled 1, 2, and 3, terminate at the distal end, "4" at the extreme distal tip, the other two at the sides (Sheet 1, FIG. 1, "4", "5", "6").

The new catheter of this application is shown in Sheet 2, FIG. 2. It terminates at the proximal end similar to the current art catheter shown in Sheet 1, FIG. 1. The new uses a "luer-lock" or similar device (Sheet 2, FIG. 1 "A") and sliding pinch locks on the I.V. tubing (Sheet 2, FIG. 2 "B").

The catheter fits inside it's casing Sheet 3, FIG. 3 and is free to rotate inside it. The catheter fits inside the casing up to it's top (Sheet 10, FIG. 10 "H") and has points around its circumference to make it easier for the operator to grasp this area and rotate the catheter in its casing.

A locking pin track (Sheet 2, FIG. 2 "E") is molded into the proximal head of the catheter. This allows a locking pin from the casing to ride in this track and prevents the catheter from separating from the casing, but allows rotation of the catheter in the casing.

The catheter has three usable lumen (labeled 1, 2, and 3) like the current art, but all terminate distally on the sides of the catheter (Sheet 2, FIG. 21 "C"). These three usable lumens exit a short distance from each other along the axis of the catheter and 120° radially from each other (Sheet 2, FIG. 2B "4", "5", "6").

In addition to lumens 1, 2, and 3, a fourth lumen runs through the entire catheter and terminates at distal tip. This lumen, labeled "7" (Sheet 2, FIG. 2B). This is the "guide wire lumen" mentioned earlier and is only used for placement of the catheter/casing assembly in the vein over a guide wire. Once the catheter/casing assembly is placed in the vein, the guide wire is withdrawn and the lumen is sealed with a simple plastic pin or plug at the proximal end (Sheet 2, FIG. 2A, "7B") and not used again.

This lumen "7" can be sized smaller in diameter than lumens 1, 2, and 3 and be made to fit only the guide wire. In addition, this lumen can terminate in a simple hole at the proximal end (Sheet 2, FIG. 2A, "7B") where the plastic plug can be inserted to seal it. In the current art, the function of the "guide wire lumen" is done by using lumen "1" (Sheet 1, FIG. 1).

Sheet 3, FIG. 3 shows the casing for the application. This casing mates with the catheter shown in Sheet 2, FIG. 2. This casing has the same holed flanges (Sheet 3, FIG. 3 "C") as the conventional catheter (Sheet 1, FIG. 1 "C") so that it can be stitched to the skin to anchor it and to prevent it from rotating with the catheter.

The witness marks "1", "12" and "123" (Sheet 3, FIG. 3) as well as two of the three "0" marks are labeled "P". Witness mark "1" represents the rotational position denoting lumen 1 open to the bloodstream, witness mark "1, 2" denotes lumen 1 and 2 open to the bloodstream, and witness mark "123" denotes all lumens open to the bloodstream.

When the catheter is rotated so that a the witness mark on the catheter (Sheet 4, FIG. 4 "G") aligns with one of the witness marks on the casing, the witness mark that is aligned will denote which lumen is open to the blood stream, i.e. when aligned with "1", lumen 1 is open; when aligned with "12" lumen 1 and 2 are open; and when aligned with "123" lumen 1, 2, and 3 are open to the bloodstream. When aligned with one of the "0" marks, all lumens are closed to the bloodstream.

When the casing/catheter is manufactured, these marks are "timed" with the lumen exit holes and casing ports so this can occur.

Sheet 3, FIG. 3A shows a top view of the casing taken along line 300 showing the locking pin collar ("F"). This holds a spring loaded pin that rides in the circular pin track on the catheter (Sheet 2, FIG. 2 "E") and keeps the catheter locked in the casing, but allows rotation of the catheter in the casing.

Sheet 3, FIG. 3B shows an enlarged view of the distal tip of the casing, taken along line 310, showing the six holes or "ports". These ports are the same size as the lumen exit holes. When the catheter is assembled in the casing, the exit holes and ports are in the same radial plane.

Ports 10, 9A and 8 are facing the viewer; ports 8A, 9A and 8B are 120° out of view and are represented by broken lines (Sheet 3, FIG. 3B). The witness marks on the casing ("P") are shown in the same plane for clarity, (Sheet 3, FIG. 3), in actuality the marks are arranged radially around the casing. "1", "12" and "123" are separated 120. The three "0" marks are between the above marks and are also 12 (7 apart as shown in Sheet 3, FIG. 3A.

When the lumen exit hole is aligned with a port, it is open to the blood stream. When the catheter is rotated so the exit holes for the lumen and the port are not aligned, the lumen is then closed to the blood stream.

Sheet 4, FIG. 4 shows the assembled catheter/casing. To operate, the user rotates the catheter by grasping the top of the catheter (Sheet 10, FIG. 10 "H") and rotating to the desired position by aligning the mark on the catheter (Sheet 4, FIG. 4 "G") to the desired witness mark (Sheet 3, FIG. 3 "P") on the casing.

Figure 5:
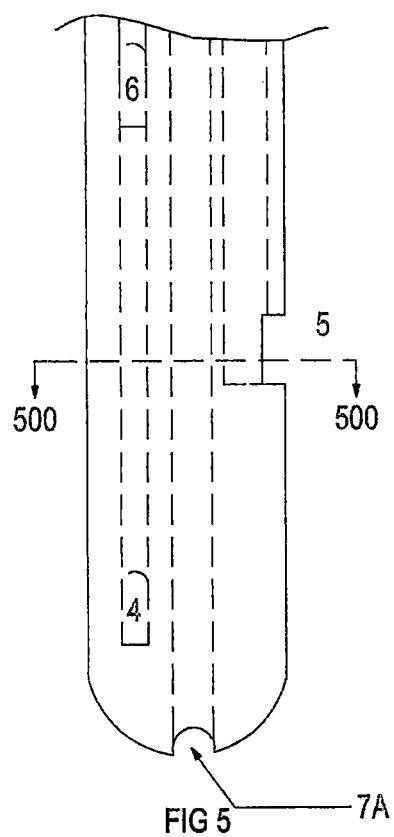
FIG. 5 shows the distal tip and the arrangements of port 4, 5, and 6.

Sheet 5, FIG. 5 shows an enlarged view of the catheter tip of the new catheter. The casing is omitted for clarity. The drawing shows the three lumen exit holes and their radial arrangement. Lumen exit hole 4 is facing the viewer, lumen 2 exit hole 5 is 120° separated from lumen exit hole 4 and lumen exit hole 6 is 120° separated from exit hole 5, and out of view, represented by broken lines.

Figure 5A:
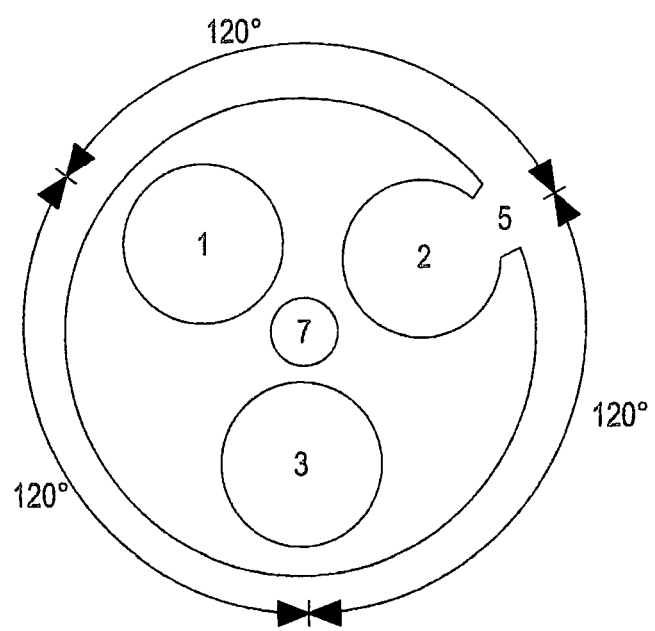
FIG. 5A shows a cross section taken along line 500 on FIG. 5 and shows the location of the infusion 1, 2 and 3 and guide wire lumen 7.

Sheet 5, FIG. 5A shows a cross section taken along line 500 through the lumen exit hole 5 showing the arrangement of lumens in the catheter body. The "guide wire lumen" is labeled "7" and exits at the distal tip. Lumen exit holes 4, 5 and 6 are separated from each other a short distance along the catheter's casing axis (proximal to distal). (Sheet 5, FIG. 5).

Figure 6:
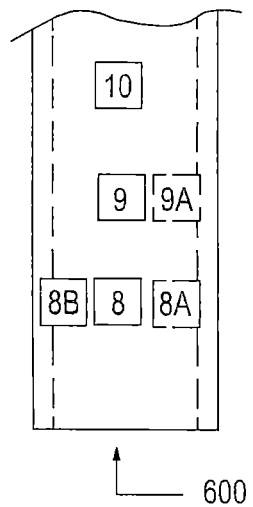
FIG. 6 shows ports 10, 9 and 8 facing the viewer. Ports 9A, 8A and 8B are 120° apart and represented by dashed lines because they would be out of view.

As stated previously the sequential opening and closing of the distal lumens is a desirable feature of this design. How this is accomplished in the rotational variant is explained in detail:

Sheet 6, FIG. 6 shows an enlarged view of the casing for the application, showing the ports at the distal tip. When the catheter is assembled in the casing the lumen exit hole 4 is on the same plane as the ports on the casing, i.e. lumen exit hole 4 is on the same plane as ports 8, 8A and 8B; lumen exit hole 5 is on the same plane as ports 9 and 9A; lumen exit hole 6 is on the same plane as port 10.

Sheet 6, FIG. 6 shows the distal tip of the casing for the application, the catheter is omitted on Sheet 6 for clarity.

Figure 6A:
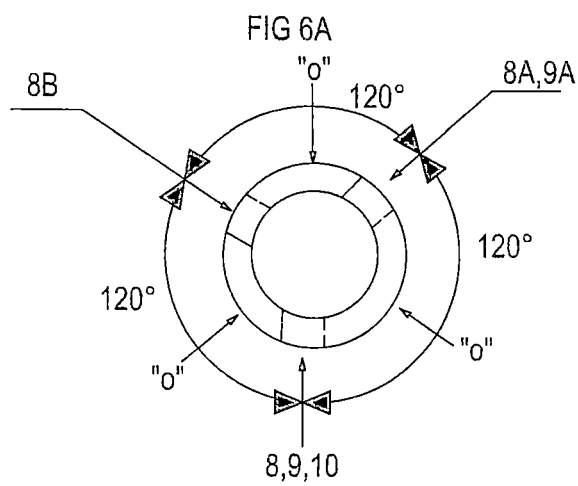
FIG. 6A shows the same view as FIG. 6 but rotated 120° to the left. Port 9A and 8A are facing the viewer, port 10, 9, 8 and 8B are now out of view and represented by dashed lines.
Figure 6B:
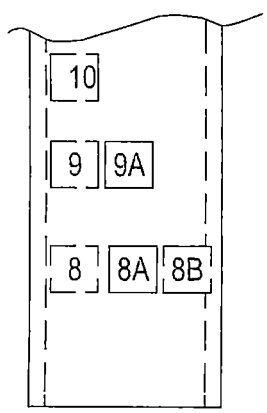
FIG. 6B shows a view taken from line 600 in FIG. 6 and shows the radial arrangements of the ports. Locations of the witness marks 0 are labeled "O".

Sheet 6, FIG. 6B shows a cross sectional view of the casing taken along line 600 showing the radial position of the ports. The "0" marks are not ports, but are the positions that the catheter is rotated to close all the lumens to the blood stream.

Sheet 6, FIG. 6 shows the casing with the ports 10, 9 and 8 facing the viewer. Port 8, 8B and 9A are 120° out of view and represented by broken lines.

Sheet 6, FIG. 6A shows the catheter rotated 120° counter clock-wise from Sheet 6, FIG. 6 with ports 8A and 9A facing the viewer, with ports 8, 9 and 10 and 8B 120° out of view.

Figure 6C:
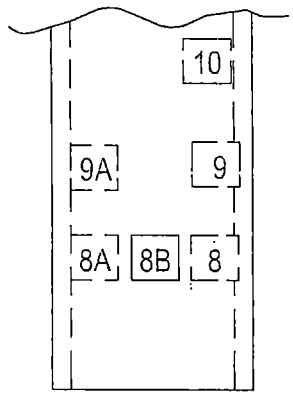
FIG. 6C shows the same view as FIG. 6 but rotated 240' to the left. Port 8B is facing the viewer, port 10, 9, 9A, 8 and 8A are now out of view and represented by dashed lines.

Sheet 6, FIG. 6C shows the catheter rotated an additional 120' counter clock-wise with port 8B facing the viewer, with ports 8, 9, 10, 8A and 9A 120° out of view.

Sheet 7, FIG. 7 shows the distal casing and catheter assembled. Sheet 7, FIG. 7 shows the casing and catheter with the ports 8, 9 and 10 facing the viewer. FIG. 7 also shows the lumens 1, 2, and 3 represented by broken lines and how their exit holes are separated along the catheter's axis with exit hole 4 most proximally; exit hole 6 most distal.

Sheet 7, FIG. 7A shows a cross section taken along line 720 through port 8, 8B and 8A. In this view, the catheter is aligned with the "1" witness mark on the casing. The catheter's lumen's exit hole 4 is aligned with port 8 and open to the bloodstream. Lumen 2 and 3 is not shown in this view because their exit holes are above this level (FIG. 7).

Sheet 7, FIG. 7B shows a cross section taken along line 710-710 through ports 9 and 9A. The catheter is in the same rotational position as FIG. 7A (the "1" position). Note that the lumen's exit hole 5 is covered by the casing and is closed to the blood stream. Lumen 3 is not shown because it terminates at a higher level proximally.

Sheet 7, FIG. 7C shows a cross section taken along line 700 through port 10. The catheter is still in the same rotational position (the "1" position) as in views FIG. 7A and FIG. 7B. Note that lumen exit hole 6 is covered by the casing and is closed to the blood stream, leaving only lumen 1 open to the bloodstream.

Sheet 8 shows the same distal and cross section views as in Sheet 7, but in this drawing the cross section views show the catheter rotated 120° from the "1" position to the "12" position.

Sheet 8, FIG. 8A shows a cross section taken along line 820 through ports 8, 8A and 8B. Note that when exit 4-4 hole has shifted to port 8A it remains open to the blood stream. As previously, lumens 2 and 3 are not shown because they terminate above this level (FIG. 8).

Sheet 8, FIG. 8B shows a cross section taken along line 810-810 through port 9 and 9A. The catheter is in the same position as in FIG. 8A (the "1, 2" position). Note that lumen exit hole 5 is now aligned with port 9 and is open to the bloodstream.

Sheet 8, FIG. 8C shows a cross section through port 10 along line 800-800. The catheter is in the same position as in FIG. 8B (the "12" position). Note that exit hole for lumen 3 is covered by the casing and closed to the blood stream, leaving only lumen 1 and 2 open to the bloodstream.

Sheet 9, FIG. 9 shows the same distal segment as in Sheet 7 and Sheet 8. In this drawing the catheter is rotated 120° clock-wise to the "123" position (witness mark).

Sheet 9, FIG. 9A shows a cross section taken along line 920-920 and the lumen exit hole 4 is now aligned with port 8B and is open to the blood steam. Once again lumen 2 and 3 are not shown, having terminated at higher levels proximally (FIG. 9).

Sheet 9, FIG. 9B shows the cross section taken along line 910-910 through the ports 9 and 9A. The catheter is at the same rotation position as FIG. 10J FIG. 9A (position 123). Note that lumen exit port 5 is now aligned with port 9A and still open to the blood stream.

Sheet 9, FIG. 9C shows the cross section taken along line 900-900 through port a 10. The catheter is in the same rotational position as FIG. 9A and FIG. 9B ("123" position). Note that the exit port 6 for lumen 3 is now aligned with port 10 and is open to the bloodstream, leaving lumen 1, 2, and 3 open to the bloodstream.

Rotating the catheter 60' to the witness mark "0" will position all the lumen ports out of alignment with the casing ports, closing all lumen to the blood stream. This completes the cycle of sequential opening of lumens 1, 2, and 3. The "guide wire lumen" is labeled "7" in Sheet 8 and Sheet 9.

Figure 10:
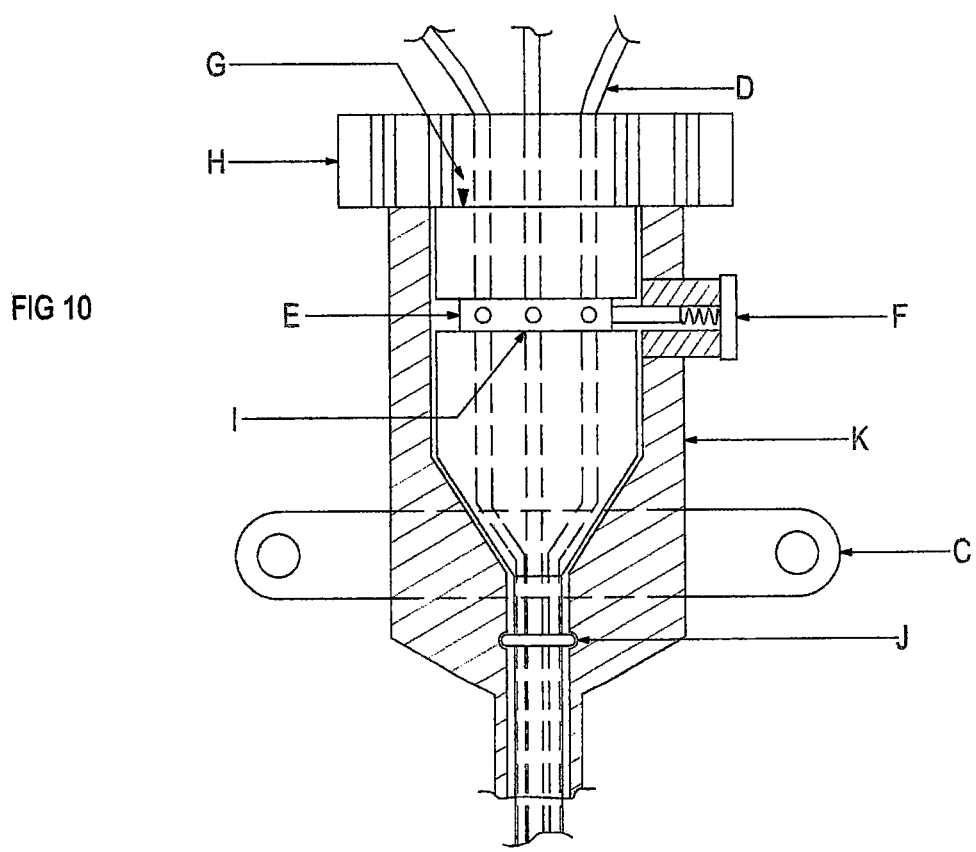
FIG. 10 shows a cutaway view of the proximal casing with the catheter seated in the casing. IV tubing is labeled "D". Luer-Locks and pinch locks are omitted for clarity. The top of the catheter is labeled "H". A witness mark on the rotating catheter is used to align with the witness mark on the casing and is labeled "G". The cutaway section of the casing is labeled "K". The O-ring seal is labeled "J". The locking circular track is labeled "E", with detents labeled "I". Locking collar with pin and spring are labeled "F" and stitch ears are labeled "C".

Sheet 10, FIG. 10 shows an enlarged view of the catheter/ casing of the application. The proximal casing head is shown in cross sections to better show how the catheter fits into the casing. The locking pin and collar, labeled "F", shows the pin is spring loaded and presses into the circular track, labeled "E", keeping the catheter and casing locked together but allowing 360' of rotation of the catheter in it's the casing. Witness mark "G" rotates with the catheter and is aligned with the witness marks on the casing by rotating the catheter in the casing.

Detents "I" are molded in the circular track. The spring loaded pin rides over these detents at the six positions to hold the catheter in the selected position and to give the operator a tactile "feel" of the catheter rotational position. These detents are timed to coincide with the positions "1", "1, 2", "1, 2, 3" and three "0" positions.

An "O" ring and seat is labeled "J". This "O" ring wipes against the catheter and is included in the design to ensure that blood plasma does not migrate out of the catheter/ casing.

It should be noted that when the catheter is in the vein the blood flow in the vein is to ward the distal end. This should cause a slight suction on the catheter/casing interface so that plasma will not migrate up in the proximal head. The "O" ring therefore may not be needed. This can only be determined in clinical trials of the new catheter.

All the text and drawings in this application show the "triple lumen type". This is because this is the most common type in use. The reason for its popularity is because the triple lumen has turned out to be the perfect because between having the right amount of usable lumens (three) and having an acceptable diameter of the catheter. If this diameter becomes too large, it becomes difficult to insert into the vein easily.

This is the primary reason why catheters of four or more lumens are virtually never used. This invention can be made to work with more than three lumens, but the diameter restrictions will apply and be made worse by the requirement for a casing, which will add to the diameter of the catheter.

This design shows the three usable lumens plus the "guide wire lumen". Despite the fact this "guide wire lumen" can be made much smaller in diameter that the three usable lumens, it may turn out that the diameter of the catheter is still considered too large but this design can be made without the "guide wire lumen" as well.

For this design to work without this "guide wire lumen" one of the usable lumen will have to terminate at the extreme distal tip, like in a conventional catheter (Sheet 1, FIG. 1). This lumen "1" can be used for the guide wire, but since it cannot interact with casing, it will always be open to the blood stream at its distal end and be subject to clotting.

The remaining lumens can still exit at the sides of the distal tip and interact with the casing to be closed distally. In the case of a triple lumen catheter, two of the three lumens will be able to close distally but the third lumen, while usable, will not be able to be closed distally.

The invention claimed is:

1. An assembly comprising:
   a catheter comprising:
      a central lumen extending along a longitudinal axis,
      three radial lumens configured to infuse fluid into a vein, the three radial lumens being radially arranged around the central lumen,
      wherein each of the three radial lumens comprises a proximal end, a distal end, a connector located at the proximal end, and an exit port located at the distal end,
      wherein each of the exit ports extends through a wall of the catheter on a distal portion of the catheter, the exit ports being spaced apart from each other both longitudinally and radially on the wall of the catheter;
a casing surrounding the catheter, the casing comprising:
   an open proximal end,
   a distal portion having multiple casing ports extending through a wall of the casing;
wherein the catheter is configured to rotate within the casing between at least three different positions;
wherein in a first position of the at least three positions, a first exit port of the exit ports is aligned with a respective one of the multiple casing ports while the rest of the exit ports are not aligned with any of the multiple casing ports;
wherein in a second position of the at least three positions, the first exit port and a second exit port of the exit ports are each aligned with a respective one of the multiple casing ports while the rest of the exit ports are not aligned with any of the multiple casing ports; and
wherein in a third position of the at least three positions; the first exit port, the second exit port, and a third exit port of the exit ports are each aligned with a respective one of the multiple casing ports;
wherein in a position between any of the at least three positions; the first exit port, the second exit port, and the third exit port of the exit ports are not aligned with any of the multiple casing ports.

* * * * *